United States Patent [19]

Schostarez

[11] Patent Number: 4,777,286

[45] Date of Patent: Oct. 11, 1988

[54] CERTAIN ARYL OR HETERO-HYDROXAMIC ACID ESTERS USEFUL AS RENIN INHIBITORS

[75] Inventor: Heinrich J. Schostarez, Portage, Mich.

[73] Assignee: The Upjohn Company, Kalamazoo, Mich.

[21] Appl. No.: 746,147

[22] Filed: Jun. 18, 1985

[51] Int. Cl.$^4$ .................. C07C 125/06; C07D 211/70; C07D 211/82; C07D 215/12

[52] U.S. Cl. .................................... 560/312; 560/158; 546/335; 546/337; 546/176; 546/149; 546/139; 546/140; 546/264; 548/491; 548/455

[58] Field of Search ................. 560/312, 158; 546/335, 546/337, 176, 149, 139, 140, 264; 548/491, 455

[56] References Cited

U.S. PATENT DOCUMENTS

| | | | |
|---|---|---|---|
| 663,027 | 10/1984 | Hester | 260/239 A |
| 4,424,207 | 1/1984 | Szelke | 260/239 A |
| 4,477,441 | 10/1984 | Boger | 260/239 A |
| 4,481,192 | 11/1984 | Cazaubon | 260/239 A |

FOREIGN PATENT DOCUMENTS 0118223  9/1984  European Pat. Off. ........ 260/239 A

OTHER PUBLICATIONS

Ann. Rev. Biochem., 51, pp. 283-308 (1982), M. A. Ondetti & D. W. Cushman, "Enzymes of the Renin ...".

J. Am. Chem. Soc., 101, p. 3983 (1979), P. G. Mattingly et al., "A Facile Synthesis of Substituted ...".

Journ. Org. Chem., 47, p. 5160 (1982), D. M. Floyd et al., "Monobactams. Preparation of (S)-3-Amino-2-Oxoazetidine-1-Sulfonic Acids ...".

Trans Biochem. Soc., 12, p. 956 (1984), D. F. Veber et al., "Renin Inhibitors ...".

Journ. Chem. Soc. Chem. Comm., p. 109 (1985) M. G. Bock et al., "Dipeptide Analogues. Synthesis of a Potent Renin Inhibitor".

J. Org. Chem., 45, p. 410 (1980) P. G. Mattingly et al., "Titanium Trichloride Reduction of Substituted N-Hydroxy-2-Azetidinones ...".

*Primary Examiner*—Alan L. Rotman
*Assistant Examiner*—Robert C. Whittenbaugh
*Attorney, Agent, or Firm*—Paul J. Koivuniemi

[57] ABSTRACT

Process and compounds for producing intermediates for the production of renin inhibitors.

5 Claims, No Drawings

CERTAIN ARYL OR HETERO-HYDROXAMIC ACID ESTERS USEFUL AS RENIN INHIBITORS

TECHNICAL BACKGROUND

1. Field of Invention

This invention relates to intermediate compounds and processes for the production of compounds useful for the preparation of renin inhibitors.

2. Information Disclosure

The renin angiotensin system is an important vasoconstrictor mechanism, and is implicated in hypertension. The end-product of this system is angiotensin II which is among the most powerful vasoconstrictor agents known. Angiotensin II is produced in a two-step process from angiotensinogen as follows:

Angiotensinogen→angiotensin I→angiotensin II.

The conversion of angiotensinogen to angiotensin I is catalyzed by renin. [For review, see M. A. Ondetti and D. W. Cushman, "Enzymes of the Renin Angiotensin System and Their Inhibitors", *Ann. Rev. Biochem.*, 51, pp. 283-308 (1982)].

To prevent the hypertensive effect of the renin-angiotensin system it would be useful to have effective renin inhibitors. Renin inhibitors are known [e.g., European patent publication, EP No. 0118223, and U.S. Pat. Nos. 4,481,192, 4,424,207 and 4,477,449]. By preventing or controlling the formation of angiotensin I from angiotensinogen with these renin inhibitors it may be possible to control unwanted levels of subsequent deleterious substances such as angiotensin II. Therefore, renin inhibitors are potentially useful for diagnosis and treatment of renin dependent hypertension and for the treatment of congestive heart failure. Renin inhibitors may also be useful in combination with other therapeutic agents such as diuretics (e.g., hydrochlorothiazide and furosemide), and vasodilators (e.g. minoxidil).

The background for the incorporation of the intermediate compounds of the instant invention into renin inhibitors can be found in U.S. patent application Ser. No. 663,027, filed on Oct. 19, 1984, which is a continuation-in-part of application Ser. No. 638,025, filed Aug. 6, 1984, and in European patent publication EP No. 0118223.

EP No. 0118223 also refers to the preparation of compounds related to the compounds of the instant application such as (3S,4S)-3-[(benzyloxycarbonyl)amino]-4-[(tert-butoxycarbonyl)amino]-6-methylheptanoic acid. No experimental details of the synthesis are reported therein.

P. G. Mattingly et al., *J. Am. Chem. Soc.*, 101, p. 3983 (1979) refers to cyclization of amides to β-lactams utilizing triphenylphosphine and DEAD. A method for reducing the β-lactam so produced is referred to in P. G. Mattingly and M. J. Miller, *J. Org. Chem.*, 45, p. 410 (1980).

D. M. Floyd et al., *J. Org. Chem.*, 47, p. 5160 (1982) refers to amide cyclization utilizing potassium carbonate to produce an azetidinone and reduction thereof.

D. F. Veber et al., *Trans. Biochem. Soc.*, 12, p. 956 (1984) and M. G. Bock et al., [*J. Chem. Soc. Chem. Comm.*, p. 109 (1985) refer to the preparation of 2-alkylated statine analogues and their incorporation into peptidic renin inhibitors.

None of the documents cited above teaches or suggests the preparation of the substituted 3,4-diamino pentanoic acid derivatives of the instant application and the intermediate compounds and processes useful in the preparation thereof.

SUMMARY OF THE INVENTION

The present invention relates to processes and intermediate compounds for the production of 3,4-diaminopentanoic acid derivatives of formula I wherein:

The stereochemistry may be R or S with any combination when multiple stereocenters are present, and wherein $R^4$ and $R^2$ are the same or different, and are
(a) hydrogen, or
(b) a nitrogen protective group;
wherein $R^3$ is
(a) hydrogen, or
(b) $C_1$–$C_4$ alkyl;
wherein $R^1$ is
(a) $C_3$–$C_8$ alkyl, including branched chain and cyclic groups, or
(b) aryl;
wherein each occurrence of $R^5$ is the same or different and is
(a) hydrogen,
(b) $C_2$–$C_9$ alkyl, including branched chain and cyclic groups,
(c) aryl-$C_1$–$C_3$-alkyl-,
(d) hydroxy-$C_2$–$C_6$-alkyl-, or
(e) ($C_3$–$C_6$ cycloalkyl)-$C_1$–$C_3$-alkyl-, comprising:
  (a) protecting the α-amino moiety of formula A-1 by reacting formula A-1 with a protecting group to produce A-2,
  (b) reducing the protected α-amino acid A-2 to the amino alcohol A-3,
  (c) oxidizing the amino alcohol A-3 to produce amino aldehyde A-4,
  (d) converting A-4 to the β-hydroxyester A-5,
  (e) hydrolyzing A-5 to the carboxylic acid A-6,
  (f) converting acid A-6 to amide A-7,
  (g) cyclizing amide A-7 to the β-lactam A-8,
  (h) reducing β-lactam A-8 to β-lactam A-9,
  (i) cleaving the lactam ring of A-9 by reacting with aqueous alcoholic solutions of excess base, and
  (j) protecting the β-amino moiety of A-10 and optionally esterifying the carboxylic acid A-10 to produce A-11.

More preferably, $R^1$ is
(a) cyclohexyl,
(b) phenyl,
(c) isopropyl,
(d) cyclopentyl, or
(e) phenyl optionally substituted with iodo, bromo, chloro, fluoro, trifluoromethyl, $C_1$–$C_3$ alkyl, hydroxy or methoxy.

When $R^5$ is aryl-$C_1$–$C_3$-alkyl-, the preferred aryl is
(a) phenyl, or
(b) phenyl optionally substituted with $CF_3$, $C_1$–$C_3$ alkyl, $OCH_3$, bromo, chloro, fluoro, iodo or hydroxy.

Also, alternatively to steps (a) and (b), the α-amino acid A-1 may be reduced to the amino alcohol using lithium aluminum hydride prior to the protection reaction of Step (a) to produce the protected amino alcohol A-3.

Also included within the invention are intermediate compounds useful for producing the compounds of formula I, including:

(A) A compound of the formula III
  wherein $R^1$ is
    (a) $C_3$–$C_8$ alkyl, including branched chain and cyclic groups, or
    (b) aryl;
  wherein $R^2$ is
    (a) hydrogen, or
    (b) a nitrogen protective group;
  wherein $R^7$ is hydroxy;
  wherein each occurrence of $R^5$ is the same or different and is
    (a) hydrogen,
    (b) $C_2$–$C_9$ alkyl, including branched chain and cyclic groups,
    (c) aryl-$C_1$–$C_3$ alkyl-,
    (d) hydroxy-$C_2$–$C_6$-alkyl-, or
    (e) ($C_3$–$C_6$ cycloalkyl)-$C_1$–$C_3$-alkyl-;
  wherein $R^8$ is —NHOR$^6$;
  wherein $R^6$ is
    (a) $C_1$–$C_6$ alkyl,
    (b) benzyl, or
    (c) aryl;
  and acid and base addition salts thereof.
(B) A compound of the formula IV
  wherein $R^1$ is
    (a) $C_3$–$C_8$ alkyl, including branched chain and cyclic groups, or
    (b) aryl;
  wherein $R^2$ is
    (a) hydrogen, or
    (b) a nitrogen protective group;
  wherein $R^9$ is
    (a) hydrogen, or
    (b) OR$^{14}$
  wherein $R^{14}$ is
    (a) hydrogen,
    (b) benzyl,
    (c) phenyl optionally substituted with $C_1$–$C_3$ alkyl, or methoxy,
    (d) $C_1$–$C_6$ alkyl, or
    (e) aryl; and
  wherein each occurrence of $R^5$ is the same or different and is
    (a) hydrogen
    (b) $C_2$–$C_9$ alkyl, including branched chain and cyclic groups,
    (c) aryl-$C_1$–$C_3$-alkyl-,
    (d) hydroxy-$C_2$–$C_6$-alkyl-, or
    (e) ($C_3$–$C_6$ cycloalkyl)-$C_1$–$C_3$-alkyl-.
(C) A compound of the formula V
  wherein $R^{10}$ is
    (a) $C_6H_5CH_2O$—,
    (b) —OH,
    (c) —OCH$_3$, or
    (d) hydrogen.
(D) A compound of formula VI
  wherein $R^{11}$ is
    (a) benzyl, or
    (b) methyl.

The compounds of formula I may also be isolated, prepared, or utilized as salts.

When $R^3$ is hydrogen, then acceptable cationic moieties include ammonium, and metal, amine, or quaternary ammonium cations.

Especially preferred metal cations are those derived from the alkali metals, e.g., lithium, sodium, and potassium, and from the alkaline earth metals e.g., magnesium and calcium, although cationic forms of other metals, e.g., aluminum, zinc, and iron are within the scope of the invention.

Acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like, aliphatic, cycloaliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, glactamine, N-methylglucosamine, ephedrine, phenylephrine, epinephrine, procaine, and the like. Further useful amine salts are the basic amino acid salts, e.g., lysine and arginine.

Examples of acceptable quaternary ammonium cations are tetramethylammonium, tetraethylammonium, benzyltrimethylammonium, phenyltriethylammonium, and the like.

When $R^3$ is other than hydrogen and $R^4$ is hydrogen, then acceptable acids for forming acid addition salts include hydrogen chloride, hydrogen bromide, hydrogen iodide, sulfuric acid, phosphoric acid, acetic acid, lactic acid, citric acid, succinic acid, benzoic acid, salicyclic acid, pamoic acid, cyclohexanesulfamic acid, methanesulfonic, naphthalenesulfonic, p-toluenesulfonic, maleic, fumaric, oxalic acids, and the like.

When $R^3$ and $R^4$ are both hydrogen, the compounds of formula I exist in zwitterionic form.

These compounds are useful intermediates for the preparation of renin inhibitors.

DETAILED DESCRIPTION

The definitions and explanations below for the terms as used throughout this entire patent application including both the specification and the claims.

All temperatures are in degrees Centigrade.
THF refers to tetrahydrofuran.
DMSO refers to dimethylsulfoxide.
DMF refers to dimethylformamide.
DCM refers to dichloromethane.
TEA refers to triethylamine.
Halogen refers to chlorine, bromine or fluorine.
IR refers to infrared spectroscopy.
UV refers to ultraviolet spectroscopy.
PMR refers to proton magnetic resonance spectroscopy, chemical shifts are reported in ppm (δ) downfield from TMS.
CMR refers to C-13 magnetic resonance spectroscopy, chemical shifts are reported in ppm (δ) downfield from TMS.
NMR refers to nuclear (proton) magnetic resonance spectroscopy, chemical shifts are reported in ppm (δ) downfield from TMS.
TMS refers to trimethylsilane.

$[\alpha]_D^{25}$ refers to the angle of rotation of plane polarized light (specific optical rotation) at 25° with the sodium D line (5893A).

MS refers to mass spectrometry.
DEAD refers to diethyl azodicarboxylate.
CBZCl refers to benzyl chloroformate.
DCHA refers to dicyclohexylamine.
Boc refers to tert-butoxycarbonyl.
CBZ refers to benzyloxycarbonyl.
Brine refers to saturated aqueous sodium chloride.
$\phi$ refers to phenyl.
h refers to hours.
$R^1-R^{14}$ are as defined in the first occurrence of each herein.

Aryl refers to phenyl, 1 or 2-naphthyl, 2,3, or 4-pyridyl, 2 through 8 quinolinyl, 1,3,4,5,6,7 or 8-isoquinolinyl, and 1 through 7-indolinyl optionally substituted with 1 to 3 of halogen (including iodine), $C_1-C_3$-alkyloxy, hydroxy-$C_1-C_3$-alkyl-, hydroxy, $C_1-C_3$-alkyl, and $CF_3$.

When the term "Cn-Cp alkyl", for example, is used, it means and includes isomers thereof where such exist.

Protective groups for nitrogen moieties are well known in many fields of organic chemistry, including peptide chemistry. Examples of nitrogen protective groups are Boc and CBZ. Other nitrogen and oxygen protective groups are set forth in T. W. Greene, *Protecting Groups in Organic Synthesis*, Wiley, New York, (1981); J. F. W. McOmie, ed. *Protective Groups In Organic Chemistry*, Plenum Press (1973); and J. Fuhrhop and G. Penzlin, *Organic Synthesis*, Verlag Chemie (1983). Included among the nitrogen protective groups are Boc, CBZ, acetyl, allyl, phthalyl, benzyl, benzoyl, trityl and other nitrogen protective groups. It should be recognized that when a free OH is present in a formula I compound, it may be necessary or desirable to protect this OH group in the synthesis of the formula I compound.

General Method for Preparing Compounds of Formula I

This general method is set forth as illustrative and the invention should not be considered to be limited by any recitation used herein.

The starting materials for preparation of compounds of formula I are α-amino acids of formula II.

A wide variety of such α-amino acids are commercially available including leucine, phenylalanine, tyrosine, isoleucine, valine, and the like in the d, l, or dl form. A number of chemical syntheses for producing such amino acids are also known, see, e.g., J. P. Greenstein and M. Winitz, *Chemistry of the Amino Acids*, Wiley, New York, p. 697 (1961); J. J. Fitt, and H. W. Gschwend, *J. Org. Chem.*, 42, p. 2639 (1977); G. Stork, A. Y. W. Leong, A. M. Touzin, *J. Org. Chem.*, 41, p. 3491 (1976); and references cited therein.

Referring now to Chart A, the general synthesis of compounds of formula I from the starting materials of formula II is as follows:

Step 1: The α-amino acid of formula A-1 (II) is protected with one of a variety of nitrogen protective groups. For example, commercially available Boc anhydride or Boc-ON (2-(t-butoxy-carbonylimino)-2-phenylacetonitrile) in water or aqueous mixtures of THF or dioxane for the former and TEA for the latter are reacted with formula A-1. Bases used for the Boc anhydride sequence included NaOH, KOH or potassium carbonate. Temperatures range from 0°–25° with reaction times of 30 min to 2 days.

Step 2: Protected α-amino acid A-2 is reduced, for example, using diborane/THF complex (H. C. Brown and D. C. S. Rao, *J. Am. Chem. Soc.*, 82, p. 681 (1960)). Suitable solvents include THF, glyme and diglyme. Temperatures of 0°–80° and reaction times of 30 min to 8 h are preferred.

Alternatively to steps 1 and 2, the α-amino acid A-1 may be reduced to an amino alcohol using, for example, lithium aluminum hydride prior to the protection reaction of Step 1 to produce the protected amino alcohol A-3.

Step 3: The protected amino alcohol A-3 is oxidized to amino aldehyde A-4, for example, using the method of K. O. Mura and D. Swern, *Tetrahedron*, 34, p. 1651 (1978) and references cited therein. One eq. of A-3 is added to a $-78°$ solution of a reagent prepared at $-78°$ from 2 eq. of oxalyl chloride and 4 eq. of DMSO. Temperatures in the range of $-78°$ to $-58°$ are preferred. DCM is the preferred solvent.

Step 4: A solution of 1 eq. of A-4 is added to a $-78°$ mixture of 1.5 eq. of lithio ethyl acetate, prepared by the addition of anhydrous ethyl acetate to a $-78°$ solution of lithium dialkylamide base. After 5–30 min, mineral acid is added (e.g., 2.5N HCl) and the β-hydroxyester A-5 is isolated as in D. H. Rich, E. T. Sun, and A. S. Bopari, *J. Org. Chem.*, 43, p. 3624 (1978). Suitable solvents are THF, glyme, and diethyl ether. Anions of other metals (e.g., magnesium) are also useful. Chromatographic separation of diasteromers may be carried out at this point.

Step 5: The β-hydroxyester A-5 is hydrolyzed, for example, using aqueous base, sodium hydroxide or potassium hydroxide, at 0°–25° for a period of 1 to 24 h to yield acid A-6. Water or aqueous mixtures of THF or dioxane are suitable solvents for this reaction.

Step 6: Amide A-7 is produced from acid A-6, for example, by using 1.2 eq. of a condensing reagent, 1.2 eq. of O-alkyl or O-benzyl hydroxylamine hydrochloride and 1 to 2 eq. of base. Suitable solvents include DCM, THF/DMF and aqueous THF or DMF, depending upon the condensation reagent employed. Temperature ranges between 0° and 40° are preferred with reaction times of 15 min–24 h.

Condensation reagent-solvent combinations include:
Method A: diethylphophoryl cyanide/TEA/DCM [S. Yamada, Y. Kasai, T. Shioiri, *Tetrahedron Lett.*, p. 1595 (1973)];
Method B: 1-methyl-2-chloropyridinium iodide/diisopropylethylamine/DCM [E. Bald, K. Saigo, T. Mukaiyama, *Tetrahedron Lett.*, p. 1163 (1975)];
Method C: 1-ethyl-3-(3'-dimethylaminopropyl)-carbodiimide in DCM or aqueous mixtures of THF/DMF or THF or DMF [M. J. Miller, et al., *J. Am. Chem. Soc.*, 102, p. 7026 (1980)]; and
Method D: 1,3-dicyclohexylcarbodiimide in DCM or THF with or without 1-hydroxybenzotriazole.
Method E: 1,1'-carbonyldiimidazole in DCM or THF.

Step 7: Amide A-7 is cyclized to the β-lactam A-8, for example, by generating a leaving group at the βposition of A-7 followed by base-induced cyclization to produce A-8.

The intermediate β-mesylate A-7a is prepared with 1.1 eq. mesyl chloride in pyridine at 0°, or by the addition of mesyl chloride to a solution of A-7 and base (e.g., TEA) in DCM, or by the addition of TEA to a solution of mesyl chloride and A-7 in DCM followed by:

Method A: cyclization of the crude product with excess potassium carbonate in refluxing acetone;

Method B: cyclization with potassium carbonate and a phase transfer catalyst in refluxing water/dichloroethylene [D. M. Floyd, et al., *J. Org. Chem.*, 47, p. 5160 (1982)].

Other methods for direct conversion of A-7 to A-8 include:

Method C: treatment of A-7 with triphenylphosphine/diethylazodicarboxylate in dry THF; or Method D: treatment of A-7 with triphenylphosphine/carbon tetrachloride/TEA/THF [M. S. Miller, et al., *J. Am. Chem. Soc.*, 102, p. 7026 (1980)]. Temperatures in the range of 20°–40° and reaction times of 1 to 2 h are suitable.

Step 8: A-8 is reduced, for example, using:

Method A: when $R^6$ is benzyl, A-8 is hydrogenated with a palladium on carbon catalyst to produce the N-hydroxy compound, followed by treatment with aqueous titanium trichloride in methanol/water at pH 7.0 [P. G. Mattingly and M. J. Miller, *J. Org. Chem.*, 45, p. 410 (1980)]; or Method B: when $R^6$ is methyl, A-8 is treated with an excess of sodium in liquid ammonia [D. M. Floyd, et al., *J. Org. Chem.*, 47, p. 5160 (1982)].

Suitable solvents for the hydrogenation at pressures of 1–6 atm of hydrogen include ethyl acetate or ethanol at 20°–25° for 1–24 h. Suitable conditions for the sodium reduction include solvents of ammonia or ammonia/dry THF mixtures, a temperature range of $-78°$ to $-33°$, and reaction times of 5 min to 2 h.

Step 9: The lactam ring of A-9 is cleaved using aqueous alcoholic solutions of excess base (e.g., potassium or sodium hydroxide) at 20°–25° for 30 min to 24 h.

Step 10: The $\beta$-amino moiety of A-10 is protected to produce A-11, wherein $R^{12}$ is a nitrogen protective group, utilizing the conditions of Step 1 and optionally esterifying the carboxylic acid A-10 by known methods to produce A-11.

Steps 9 and 10 may also be carried out sequentially in the same reaction vessel by introducing the protecting reagent into the basic solution of A-10.

Referring now to Chart B, the preparation of the proper intermediates which are then incorporated into the chemistry of Chart A to prepare the 2-substituted-3,4-diamino pentanoic acid derivatives of formula I, is shown.

Step 1a: The $\beta$-hydroxy ester B-1 (A-5) is alkylated by the addition of ester B-1 (A-5) to a $-78°$ to $-20°$ solution of lithium dialkylamide base (2–4 eq.) followed by the addition of the electrophile (e.g., benzyl, allyl, or alkyl halide, an $\alpha,\beta$-unsaturated ester or ketone, substituted aldehydes) [G. Frater, *Helv. Chim. Acta.*, 62, p. 2825 (1979)]. Suitable solvents include diethyl ether, THF and dimethoxyethane.

Step 1b: Repeat Step 1a to produce B-3.

Step 2a: The $\beta$-Lactam B-4 (A-8) alkylated by adding B-4 (A-8) to a $-78°$ solution of lithium dialkylamide base followed by the addition of an electrophile (as in Step 1) [T. Durst and M. J. Labelle, *Can. J. Chem.*, 50, p. 3196 (1972)]. Suitable solvents include THF, diethyl ether, and dimethoxyethane.

Step 2b: Repeat Step 2(a) to produce B-6.

For all steps, the addition of hexamethylphosphorus triamide may improve the overall yield for that step.

In order that this invention may be better understood, the following examples are set forth. These examples are for purposes of illustration only and this invention should not be considered to be limited by any recitation used herein.

EXAMPLE 1

(3R,4S)-3-Hydroxy-4-[(tert-butoxycarbonyl)amino]-6-methylheptanoic acid (C-2)

Refer to Chart C (conversion of C-1 to C-2).

A solution of ethyl (3R,4S)-3-hydroxy-4-[(tert-butoxycarbonyl)amino]-6-methylheptanoate, [D. H. Rich, E. T. Sun and A. S. Boparai, *J. Org. Chem.*, 43, p. 3624 (1978)] (2.1 g) and potassium hydroxide (10.4 ml 1.0N solution) in THF is stirred at 20°–25° for 2.5 h. The mixture is acidified and extracted with DCM, followed by drying with anhydrous magnesium sulfate, and concentrating produces C-2 as a solid, m.p. 136°–7° d (from ethyl acetate/hexane), $[\alpha]_D^{25}$ $-25.3°$ (c 0.889, MeOH); IR (mull, cm$^{-1}$) 3355, 2952, 1714, 1700, 1684, 1530, 1449, 1304, 1275, and 1180; PMR (200 MHz, CDCl$_3$, $\delta$) 4.74, 4.08–3.89, 3.77–3.51, 2.50, 1.78–1.56, 1.31, 1.45, 0.92; CMR (CDCl$_3$, ppm) 176.31, 156.82, 80.13, 71.48, 53.13, 39.07, 37.96, 28.41, 24.81, 23.66, 21.56; MS (Cl, CH$_4$, m/z) 276, 451, 277, 204, 176.

EXAMPLE 2

Benzyl-(3R,4S)-3-hydroxy-4-[(tert-butoxycarbonyl)amino]-6-methylheptanhydroxamate (C-3)

Refer to Chart C (Conversion of C-2 to C-3).

A solution of C-2 (1.0 g) and O-benzylhydroxylamine hydrochloride (0.87 g) in THF/water (1:1, 40 ml, pH 4.75) is stirred at 20°–25° under argon and 1-ethyl-3-[3'-(dimethylamino)propyl]carbodiimide (1.4 g) is added in one portion. The pH of the solution is maintained at 4.75 and the reaction mixture is stirred for 2 h. The products is extracted into ethyl acetate and the combined organic layers are dried using anhydrous sodium sulfate and concentrated. Following chromatography on silica gel (elution with ethyl acetate-hexane, 3:2), C-3 is obtained as a solid, m.p. 131°–3° (ethyl acetate): $[\alpha]_D^{25}$ $-21.1°$ (c 0.825, MeOH); IR (mull, cm$^{-1}$) 3368, 3229, 2923, 1686, 1657, 1524, 1366, 1171; PMR (200 MHz, CDCl$_3$, $\delta$) 9.21, 7.38, 4.92, 4.60–4.46, 4.20, 3.86–3.70, 3.70–3.50, 2.24, 1.76–1.50, 1.43, 1.43–1.21, 0.93; 0.89; CMR (CDCl$_3$, ppm) 170.16, 156.79, 135.44, 129.19, 128.59, 79.91, 78.28, 53.45, 39.39, 36.78, 28.40, 24.82, 23.63, 21.60; MS (EI, m/z) 380, 91, 86, 57, 130.

EXAMPLE 3

(4S,1'S)-1-Benzyloxy-4-[1'-(tert-butoxycarbonyl)amino-3'-methylbutyl]-2-azetidinone (C-4)

Refer to Chart C (Conversion of C-3 to C-4).

A solution of C-3 (3.34 g) and triphenylphosphine (2.54 g) under argon in dry THF (100 ml) is stirred at 20°–25° and diethylazodicarboxylate (2.77 ml) is added slowly over a period of 10 min. The reaction mixture is stirred for 30 min, poured into brine and extracted with ethyl acetate. The organic layers are combined, dried using anhydrous sodium sulfate, and concentrated to give a residue which is chromatographed on silica gel (elution with ethyl acetate-hexane, 1:3) to give C-4 as an oil which crystallizes on standing: $[\alpha]_D^{25}$ $-46.1°$ (c 0.112, MeOH); IR (film, cm$^{-1}$) 2957, 1775, 1709, 1523, 1507, 1502, 1367, 1249, and 1168. PMR (200 MHz, CDCl$_3$, $\delta$) 7.41, 4.96, 4.28, 3.94–3.77, 2.61, 2.46, 1.63–1.04, 1.42, 0.88; CMR (CDCl$_3$, ppm) 165.18, 155.94, 134.98, 129.75, 129.21, 128.75, 79.65, 77.93, 60.57, 48.97, 42.32, 34.99, 28.33, 24.82, 23.12, 21.68; MS (CI, NH$_3$, m/z) 380, 52, 35, 742, 381.

EXAMPLE 4

(4S,1'S)-1-Hydroxy-4-[1'-(tert-butoxycarbonyl)amino-3'-methylbutyl]-2-azetidinone (C-5)

Refer to Chart C (Conversion of C-4 to C-5).

A solution of C-4 (2.12 g) and 10% palladium on carbon (30 mg) in anhydrous ethanol is shaken under a hydrogen atmosphere (40 psi) for 2 h. The reaction mixture is filtered and concentrated to produce C-5 as an oil: $[\alpha]_D^{25}$ −54.1° (c 0.575, MeOH); IR (film, cm$^{-1}$) 3339, 3256, 2958, 1757, 1711, 1694, 1525, 1367, 1167; PMR (200 MHz, CDCl$_3$, δ) 9.40, 5.08, 4.98–4.80, 2.72, 2.51, 1.82–1.52, 1.52–1.30, 1.44, 0.94; MS (CI, NH$_3$, m/z) 290, 291, 69, 274, 562.

EXAMPLE 5

(4S,1'S)-4-[1'-(tert-Butoxycarbonyl)amino-3'-methylbutyl]-2-azetidinone (C-6)

Refer to Chart C (Conversion of C-5 to C-6).

A solution of C-5 (240 mg) in methanol-water (1:1, 10 ml) is stirred at 20°–25° and aqueous titanium trichloride (0.30 ml, 20% solution) is added with the pH maintained at 7.0 by adding 1N sodium hydroxide. The reaction mixture is stirred for 2 h and extracted with ethyl acetate. The organic layers are combined, dried using anhydrous sodium sulfate, and concentrated to give a residue which is chromatographed on silica gel (elution with ethyl acetate) to deliver C-6 as an oil: $[\alpha]_D^{25}$ −26.6° (c 1.09, MeOH); IR (film, cm$^{-1}$) 3317, 2956, 1761, 1707, 1685, 1535, 1367, 1252; PMR (80 MHz, CDCl$_3$, δ) 6.15, 4.53, 4.03–3.53, 2.89, 2.77, 1.90–1.58, 1.44–1.11, 1.44, 0.93; MS (CI, NH$_3$, m/z) 274, 69, 124, 218, 94. Precise mass found: 256.1794.

EXAMPLE 6

(3S,4S)-3-[(Benzyloxycarbonyl)amino]-4-[(tert-butoxycarbonyl)amino]-6-methylheptanoic acid (C-7)

Refer to Chart C (Conversion of C-6 to C-7).

A solution of C-6 (466 mg) and potassium hydroxide (10 ml, 1N) in methanol (10 ml) is stirred at room temperature for 3 h, cooled to 0°, neutralized with 6N HCl, and concentrated in vacuo. The residue is taken up in potassium carbonate solution (10 ml, 1M), DMF (5 ml) is added and the solution is cooled to 0°. CBZCl (0.64 ml) is added via syringe and the reaction mixture stirred at 0° for 4 h. The ice bath is removed and the reaction mixture stirred for 2 days at 2°–25°. The pH of the reaction mixture is lowered to 2 with 6N HCl followed by extraction with DCM, drying with anhydrous magnesium sulfate, and concentration to deliver C-7 as an oil. IR (film, cm$^{-1}$) 3310, 2940, 1690, 1500, 1230 and 1150; PMR (80 MHz, CDCl$_3$, δ) 9.24, 7.30, 6.86–5.36, 5.07, 5.08–4.50, 4.22–3.47, 2.64–2.37, 1.70–0.79, 1.39 and 0.87; MS (EI) 91, 86, 54, 186, 139, 408.

EXAMPLE 7

(3S,4S)-3-[(Benzyloxycarbonyl)amino]-4-[(tert-butoxycarbonyl)amino]-6-methyl-heptanoic acid dicyclohexylamine salt (C-8)

Refer to Chart C (Conversion of C-7 to C-8).

A solution of C-7 (1.44 g) is stirred at 20°–25° in diethyl ether (20 ml) under argon and freshly distilled dicyclohexylamine (905 mg) is added via syringe. The resulting solution is stirred at 20°–25° overnight and the product is filtered and dried to produce C-8 as a solid, m.p. 150°–152° C. (ethyl acetate): $[\alpha]_D^{25}$ −28.5° (c 0.789, MeOH); IR (mull, cm$^{-1}$) 3324, 2923, 1723, 1713, 1538, 1451 and 1255; MS (CI, NH$_3$, m/z) 426, 275, 182, 427, 308.

In a similar manner starting with other diastereomers of the formula C-1 (prepared as in Chart A, Steps 1 through 4), the procedures of Chart C and Examples 1 through 7 are used to produce other corresponding diastereomers of compounds C-7 and C-8.

Likewise using other amino acid starting materials of the formula A-1 of the compounds of the formula I are prepared using the methods described herein.

Referring now to Chart D, the synthesis of (4S,1'S)-4-[1'-(tertbutoxycarbonyl)amino-3'-methylbutyl]-2-azetidinone from (3R,4S)-3-hydroxy-4-[tert-butoxycarbonyl)amino]-6-methylheptanoic acid is alternatively and preferably carried out as described in Examples 8–10 below.

EXAMPLE 8

Methyl-(3R,4S)-3-hydroxy-4-[(tert-butoxycarbonyl)amino]-6-methylheptanhydroxamate (D-2)

Refer to Chart D (Conversion of D-1 to D-2). cl (A) Diethylphosphoryl Cyanide Method A solution of D-1 (C-2) (5.0 g), methoxylamine hydrochloride (1.67 g), and diethylphosphoryl cyanide (3.26 g) in DCM (100 ml) is stirred at 0° under argon. TEA (5.31 ml) is added via syringe over a period of 5 min. The reaction mixture is stirred at 0° for 60 min, poured into water, washed with brine, dried with anhydrous sodium sulfate and concentrated to give a crude crystalline product. Recrystallization of the residue from diethyl ether gives D-2 as a solid, m.p. 134°–5° C.: $[\alpha]_D^{25}$ −13.5° (c 0.892, MeOH); IR (cm$^{-1}$ mull) 3334, 3270, 3040, 1680, 1668, 1535, 1389, 1174; PMR (80 MHz, CDCl$_3$, δ) 9.42, 4.57, 3.78–3.48, 3.77, 3.48–2.93, 2.30, 1.60–0.91, 1.44, 0.92; MS (CI, Isobutane, m/z) 305, 249, 609, 306, 289.

(B) N-Methyl-2-chloropyridinium Iodide Method

A solution of D-1 (555 mg), methoxylamine hydrochloride (200 mg), N-methyl-2-chloropyridinium iodide (612 mg), and diisopropylethylamine (1.70 ml) in DCM (10 ml) under argon is refluxed for 2 h and allowed to cool to 20°–25°. The reaction mixture is poured into brine, extracted with ethyl acetate, dried with anhydrous sodium sulfate, and concentrated. Chromatography of the residue on silica gel (elution with ethyl acetate) gives a solid D-2.

(C) 1-Ethyl-3-(3'-dimethylaminopropyl)carbodiimide Method

A solution of D-1 (1.5 g) and methoxylamine hydrochloride (0.68 g) in DMF/water/THF (40 ml, 1:2:1) is stirred at 20°–25° and the pH is adjusted to 4.25 with the addition of 1N NaOH. A solution of 1-ethyl-3-(3'-dimethylaminopropyl)carbodiimide (2.1 g, 11.0 mmole) in water is then added and the pH maintained at 4.25 with the addition of 1N HCl or 1N NaOH as required. After 2 h, the reaction mixture is diluted with water, extracted with ethyl acetate, and the organic layers are combined, dried with anhydrous sodium sulfate, and concentrated. Recrystallization of the residue from diethyl ether yields D-2 as a solid.

EXAMPLE 9

(4S,1'S)-1-Methoxy-4-[1'-(tert-butoxycarbonyl)amino-3'-methylbutyl]-2-azetidinone (D-3)

Refer to Chart D (Conversion of D-2 to D-3).

(A) DEAD-Triphenylphosphine

A solution of D-2 (304 mg) and triphenylphosphine (524 mg) in dry THF (5 ml) is stirred at room temperature under argon and DEAD (0.32 ml, 4 mmole) is added via syringe. The solution warms upon addition of DEAD and is allowed to cool to 20°-25° over a period of 30 min. The reaction mixture is concentrated in vacuo, and the residue chromatographed on silica gel (elution with ethyl acetate/hexane, 1:2) to deliver D-3 as a solid, m.p. 96.5-97.5° (hexane/diethyl ether): $[\alpha]_D^{25}$ −76.2° (c 0.795, MeOH); IR (cm$^{-1}$, mull) 3348, 2951, 1797, 1792, 1682, 1537, 1250, 1176; PMR (80 MHz, CDCl$_3$ δ) 4.55–4.17, 4.17–3.60, 3.78, 2.60, 2.56, 1.88–1.09, 1.43, 0.94; MS (Cl, NH$_3$, m/z) 248, 304, 204, 266, 305.

(B) Carbon Tetrachloride-Triphenylphosphine

A solution of D-2 (304 mg), carbon tetrachloride (0.19 ml, 2 mmole), triphenylphosphine (524 mg), and TEA (0.28 ml) in dry THF (5 ml) is stirred under argon for 4 days. The reaction mixture is diluted with hexane (5 ml), filtered through a short silica column (elution with ethyl acetate/hexane, 1:1), and the filtrate concentrated. Chromatography of the residue on silica gel (elution with hexane/ethylacetate, 2:1) delivers D-3 as a solid.

(C) Mesyl Chloride-Pyridine

A 0° of D-2 (304 mg) in pyridine (5 ml) is stirred under argon and mesyl chloride (137 mg) is added via syringe. The reaction mixture is stirred at 0° for 2 h, poured into water, and extracted with ethyl acetate. The extracts are washed with 1N HCl and brine, dried with anhydrous sodium sulfate, and concentrated.

The residue is dissolved in acetone (30 ml), anhydrous potassium carbonate (552 mg) added and the resulting slurry refluxed for 72 h. The reaction mixture is allowed to cool to 20°-25°, diluted with ethyl acetate, and filtered. The filtrate is concentrated and the residue chromatographed on silica gel (elution with hexane/ethyl acetate, 2:1) to give D-3 as a solid.

EXAMPLE 10

(4S,1'S)-4-[1'-(tert-butoxycarbonyl)amino-3'-methylbutyl]-2-azetidinone (D-4)

Refer to Chart D (conversion of D-3 to D-4).

Sodium (75 mg) is added to a −78° solution of dry ammonia (20 ml) and the mixture is stirred for 15 min until all the metal dissolves. A solution of D-3 (200 mg) in dry THF (5 ml) is slowly added and the reaction mixture allowed to warm to reflux (−33°). After 30 min, solid ammonium chloride (200 mg) is added, and the resulting solution is allowed to warm to 20°-25° over a period of 2 h. The residue is diluted with ethyl acetate (50 ml), washed with water, dried with anhydrous sodium sulfate, and concentrated to deliver D-4 (C-6) as an oil which crystallizes on standing.

The procedures of Examples 8-10 are likewise carried out for other diastereomers prepared according to Chart A above.

FORMULAS

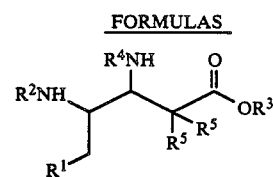

I

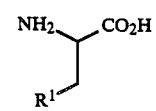

II

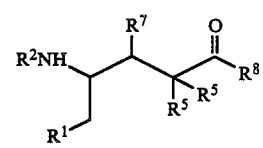

III

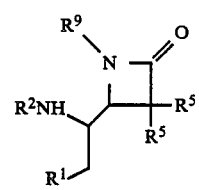

IV

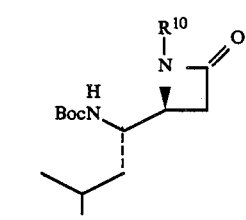

V

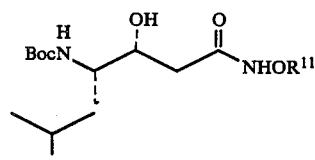

VI

CHART A

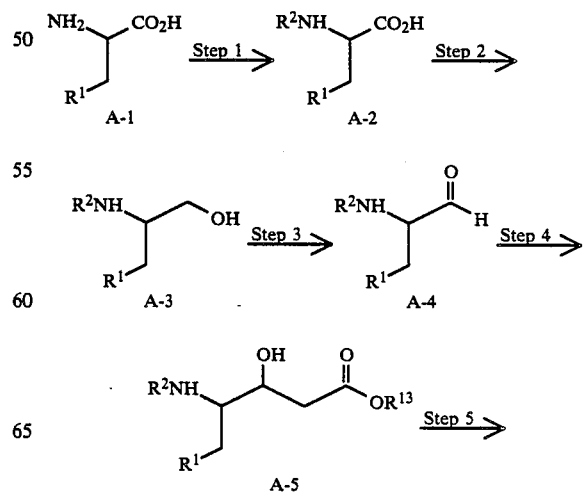

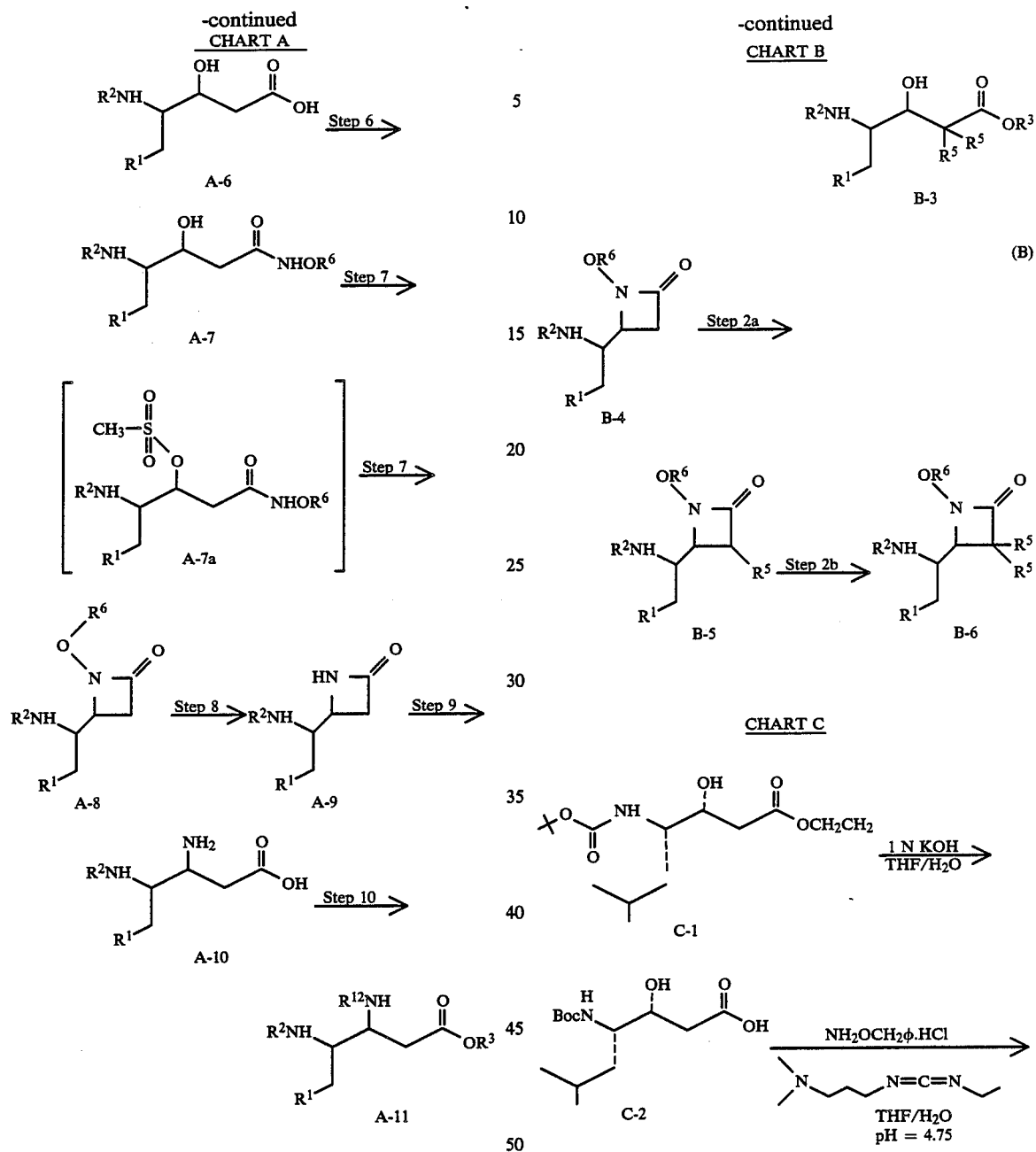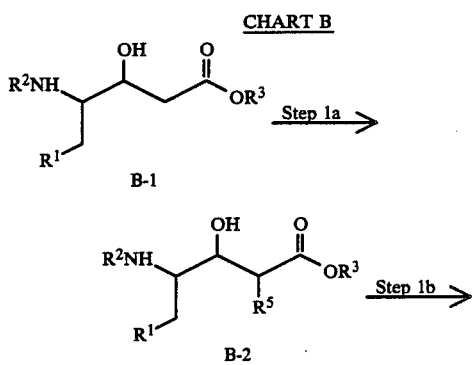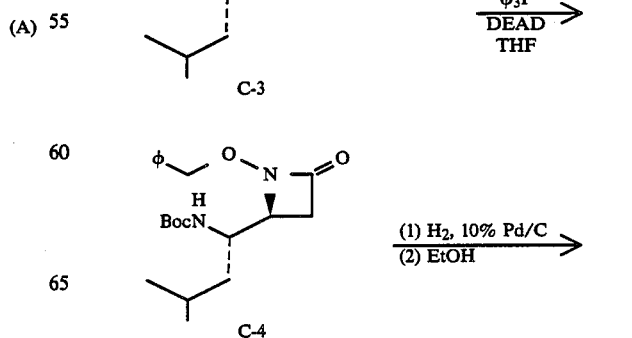

-continued
CHART C

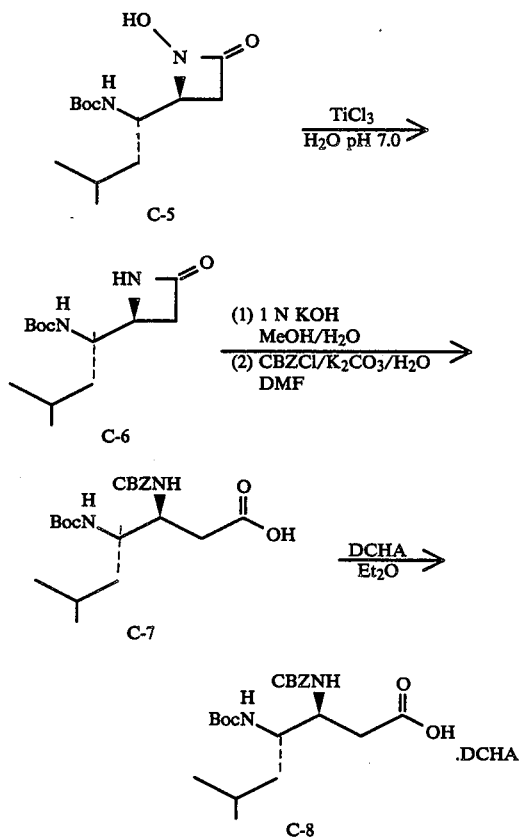

CHART D

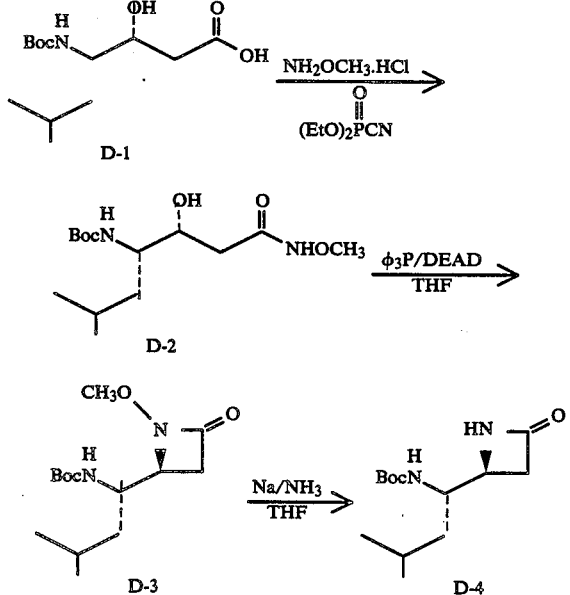

I claim:
1. A compound of the formula III

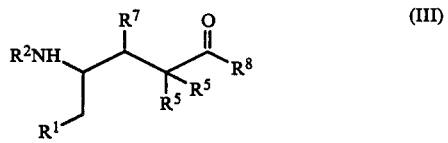

wherein $R^1$ is
   (a) $C_3$–$C_8$ alkyl, including branched chain and cyclic groups, or
   (b) aryl selected from the group consisting of phenyl, 1 or 2-naphthyl, 2,3, or 4-pyridyl, 2-8-quinolinyl, 1, 3, 4, 5, 6, 7 or 8-isoquinolinyl, and 1-7-indolinyl optionally substituted with 1 to 3 of halogen (including iodine), $C_1$–$C_3$-alkyloxy, hydroxy-$C_1$–$C_3$-alkyl-, hydroxy, $C_1$–$C_3$-alkyl, and $CF_3$;
wherein $R^2$ is
   (a) hydrogen, or
   (b) a nitrogen protective group;
wherein $R^7$ is hydroxy;
wherein each occurrence of $R^5$ is the same or different and is
   (a) hydrogen,
   (b) $C_2$–$C_9$ alkyl, including branched chain and cyclic groups,
   (c) aryl-$C_1$–$C_3$-alkyl- wherein aryl is phenyl, 1 or 2-naphthyl, 2,3, or 4-pyridyl, 2-8-quinolinyl, 1, 3, 4, 5, 6, 7 or 8-isoquinolinyl, and 1-7-indolinyl optionally substituted with 1 to 3 of halogen (including iodine), $C_1$–$C_3$-alkyloxy, hydroxy-$C_1$–$C_3$-alkyl-, hydroxy, $C_1$–$C_3$-alkyl, or $CF_3$,
   (d) hydroxy-$C_2$–$C_6$-alkyl-, or
   (e) ($C_3$–$C_6$ cycloalkyl)-$C_1$–$C_3$-alkyl-;
wherein $R^8$ is —$NHOR^6$;
wherein $R^6$ is
   (a) $C_1$–$C_6$ alkyl,
   (b) benzyl, or
   (c) aryl wherein aryl is phenyl, 1 or 2-naphthyl, 2,3, or 4-pyridyl, 2-8-quinolinyl, 1, 3, 4, 5, 6, 7 or 8-isoquinolinyl, and 1-7-indolinyl optionally substituted with 1 to 3 of halogen (including iodine), $C_1$–$C_3$-alkyloxy, hydroxy-$C_1$–$C_3$-alkyl-, hydroxy, $C_1$–$C_3$-alkyl, or $CF_3$; and acid and base addition salts thereof.

2. A compound according to claim 1, wherein $R^5$ is hydrogen and wherein $R^1$ is aryl which is phenyl optionally substituted with iodo, bromo, chloro, fluoro, trifluoromethyl, $C_1$–$C_3$ alkyl, methoxy, or hydroxy.

3. A compound according to claim 1, wherein $R^5$ is hydrogen and wherein $R^1$ is cyclohexyl optionally substituted with fluoro, trifluoromethyl, $C_1$–$C_3$ alkyl, methoxy, or hydroxy.

4. A compound selected from the group consisting of benzyl-(3R,4S)-3-hydroxy-4-[(tert-butoxycarbonyl)amino]-6-methylheptanhydroxamate, and methyl-(3R,4S)-3-hydroxy-4-[(tert-butoxycarbonyl)amino]-6-methylheptanhydroxamate.

5. (3S,4S)-3-[(Benzyloxycarbonyl)amino]-4-[(tert-butoxycarbonyl)amino]-6-methylheptanoic acid dicyclohexylamine salt.

* * * * *

UNITED STATES PATENT OFFICE
CERTIFICATE OF CORRECTION

Patent No. 4,777,286          Dated    October 11, 1988

Inventor(s) Heinrich J. Schostarez

It is certified that error appears in the above-identified patent and that said Letters Patent is hereby corrected as shown below:

Column 5, line 68, "included" should read --include--
Column 8, line 37, "products" should read --product--
Column 10, line 13, "A-1 of the compounds" should read --A-1 all of the compounds--
Column 10, line 26, "cl" should be deleted.
Column 11, line 36, "0° of D-2" should read --0° solution of D-2--
Column 13, line 51, "$P R^{13}$" should read --$R^{13}$--
Column 14, line 36, "$OCH_2CH_2$" should read --$OCH_2CH_3$--

Signed and Sealed this

Tenth Day of April, 1990

Attest:

HARRY F. MANBECK, JR.

*Attesting Officer*      *Commissioner of Patents and Trademarks*